United States Patent [19]

Dugat

[11] 3,997,506
[45] Dec. 14, 1976

[54] ANTI-MITOTIC AND ANTI-GOUT DERIVATIVES OF THIOCOLCHICINE
[75] Inventor: Pierre Dugat, Paris, France
[73] Assignee: Societe d'Etudes Chimiques an abrege Socechim, Luxembourg, Luxembourg
[22] Filed: July 7, 1975
[21] Appl. No.: 593,863
[30] Foreign Application Priority Data
July 4, 1974    United Kingdom ............ 29746/74
[52] U.S. Cl. .......................... 260/557 B; 260/571; 424/320; 424/330
[51] Int. Cl.² ................ C07C 103/19; C07C 97/16; A61K 31/16
[58] Field of Search ................. 260/557 B; 424/320
[56] References Cited
UNITED STATES PATENTS
3,657,273    4/1972    Krimmel .................... 260/557 B X OTHER PUBLICATIONS
Velluz et al., CA 49:11614d (1955).
Sandoz Ltd., CA 60:15929b (1963).
Sandoz Ltd. (Sigg), CA 61:10728h (1963).
Morrison and Boyd, Organic Chemistry, 3rd ed., p. 746, (1974).

Primary Examiner—Daniel E. Wyman
Assistant Examiner—Thomas A. Waltz
Attorney, Agent, or Firm—Haseltine, Lake & Waters

[57] ABSTRACT

The invention is concerned with novel thiocolchicine derivatives of formula:

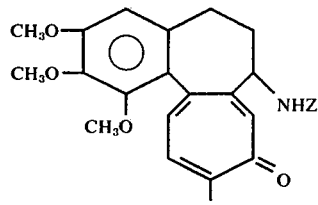

wherein Z is H or the group

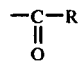

wherein R is an organic radical. The derivative wherein Z is H is prepared by hydrolyzing thiocolchicine in an aqueous acidic medium and those wherein Z is

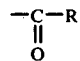

is prepared by reacting the derivative wherein Z is H with a compound of formula RCOX or

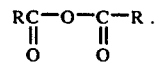

The derivative wherein R is an adamantyl group has therapeutical properties.

3 Claims, No Drawings

ANTI-MITOTIC AND ANTI-GOUT DERIVATIVES OF THIOCOLCHICINE

The present invention is concerned with certain novel thiocolchicine derivatives as well as their process of manufacture.

More specifically this invention is concerned with N-desacetyl-thiocolchicine of formula:

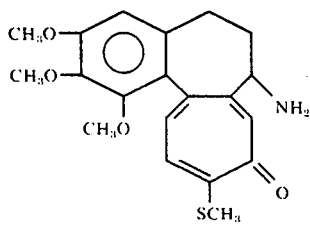

(A)

and with the N-desacetyl derivatives of the generic formula:

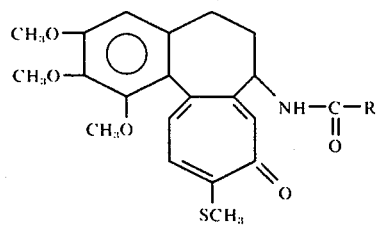

(B)

wherein R is an acyclic, heterocyclic or homocyclic radical, more particularly an aliphatic, cycloaliphatic or aromatic radical, said broad class of compounds having useful pharmacological properties as well as the above N-desacetyl-thiocolchicine.

The first new compound of the invention, i.e. N-desacetyl-thiocolchicine (A) melts at 193°–194° C and has a specific rotation $[\alpha]_D^{20}$ equal to −194.8° (in chloroform; concentration: 0.539 gr/l). Said compound may be prepared, according to the invention, by hydrolysing thiocolchicine in an aqueous acidic medium.

A particularly useful compound of formula (B), owing to its pharmacological properties, is N-desacetyl-N-adamantoyl-thiocolchicine of formula:

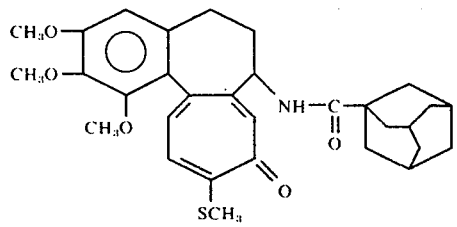

(B₁)

Said thiocolchicine derivative melts at 272.5°–273.5° C and has a specific rotation $[\alpha]_D^{20}$ equal to −200.0° (in chloroform; concentration: 0.500 gr/l).

Another object of the invention is the application of N-desacetyl-thiocolchicine to the manufacture of compounds (B) by reacting N-desacetyl-thiocolchicine with a corresponding carboxylic acid halide R COX wherein X is a halogen and R has the above meaning, preferably an acid chloride. According to another embodiment, an anhydride of a carboxylic acid, of formula

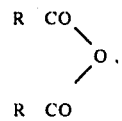

may be substituted for the aforesaid acid halide. The reaction may be effected in a suitable organic solvent such as pyridine, for example.

A further object of the present invention is constituted by medicines the pharmacological properties of which are described hereafter. The active component of such medicines is N-desacetyl-N-adamantoyl-thiocolchicine which is generally used in conjunction with a conventional vehicle, support or diluent. These medicines are notably useful for the treatment of gout or arthrolithiasis and of neoplastic diseases as well as an anti-inflammatory agent.

The invention will be more particularly illustrated by the following examples concerning preferred processes of manufacturing the above colchicine derivatives.

EXAMPLE 1 — Preparation of thiocolchicine

In a glass autoclave cooled at −30° C there were charged 34.0 g of colchicine, 6.7 g of p-toluene-sulfonic acid and 208 g of methylmercaptan. The temperature is raised up to +20° C, which causes the internal pressure of the autoclave to reach about 3 atmospheres. The reaction mixture is maintained under stirring for 10 days in the absence of light. The methylmercaptan in excess is distilled off between 20° and 40° C and the residue is treated by 670 ml of chloroform. The solution thus obtained is filtered and the filtrate is neutralized using hydrogen sodium carbonate after having added thereto 270 ml of water. The aqueous phase is separated and extracted three times with fresh chloroform. The chloroform extracts are combined, dried and evaporated. The solid residue (43 g) is dissolved in 150 ml of ethyl acetate and a few thiocolchicine crystals (obtained in a preliminary experiment) are introduced into the solution in order to initiate the crystallization. 16.0 g of thiocolchicine are collected in this manner. The mother-liquors are evaporated to give 21 g of an impure product which is subjected to a purification step by column chromatography using neutral alumina (activity I) as absorbent and chloroform as eluant. 7.1 g are thus recovered. The total amount of the desired product is 23.1 (yield: 65 %). Said yields may be improved by chromatographic purification of the above crystallization mother-liquors. The product melts at 192° C and has a specific rotation $[\alpha]_D^{20}$ equal to −229° (in chloroform; concentration: 0.524 gr/l).

EXAMPLE 2 — Preparation of N-desacetyl-thiocolchicine

A mixture containing 16.3 g of thiocolchicine, 200 ml of methanol and 200 ml of aqueous HCl (2N) is heated under reflux. The hydrolysis reaction which occurs is complete at the end of a period of time of 28 hours. 215 ml of aqueous methanol are then distilled off and the remaining aqueous solution extracted 3 times with 300 ml of chloroform. The chloroform extracts are combined and the mixture thereof washed 4 times with 300 ml of water. The remaining part of the aforesaid aqueous solution and the aqueous washing solutions are combined and alcalinized to pH13 by adding aqueous sodium hydroxide 10N. The desired product passes into the form of the free amine and is extracted using 5 portions of 300 ml of chloroform. The chloroform extracts are combined, washed with water until neutrality and dried. After evaporation of the solvent, the amine is recrystallized from a mixture chloroform (65ml)-ether (390 ml) to give 11.9 g of the product (yield 79 %).

EXAMPLE 3 — Preparation of N-desacetyl-N-adamantoyl-thiocolchicine

A solution of 9 g of N-desacetyl-thiocolchicine in 95 ml of anhydrous pyridine is cooled at 0° C. Then, 8.9 g of adamantane-carboxylic acid chloride dissolved in 15 ml of anhydrous pyridine, are added to the aforesaid solution and the temperature is maintained at 0° C. The reaction mixture is maintained under stirring for 2 hours at the ambient temperature and then, after having checked by thin layer chromatography the total absence of N-desacetyl-thiocolchicine in the mixture, the latter is diluted with 150 ml of water and 500 ml of chloroform. The solution thus obtained is successively extracted 3 times with 250 ml of aqueous HCl (2N), with water, twice with 100 ml of aqueous Na OH (N) and finally with water until neutrality. The chloroform is dried and evaporated and the residue is recrystallized in ethyl acetate. 13.55 g of yellow crystals are obtained. They contain 1 mole of ethyl acetate of crystallization for 1 mole of the product which corresponds to a yield of 90 %. Said crystals melt at 272°–273.5° C and have a specific rotation $[\alpha]_D^{20}$ equal to −169.5° C (in chloroform; concentration: 0.472 gr/l).

By distilling said crystals under vacuum ($10^{-2}$–$10^{-3}$ mm Hg) at 200° C, the pure product (without the solvation component, i.e. ethyl acetate) is obtained. Said product may be recrystallized from a mixture chloroform-hexane.

Pharmacological properties of N-desacetyl-N-adamantoyl-thiocolchicine

N-desacetyl-N-adamantoyl-thiocolchicine has an anti-mitotic activity, an anti-neoplastic activity as well as anti-inflammatory properties and is notably useful against arthrolithiasis or gout ($LD_{50}$ is about equal to 3 g/kg of the weight of the body of animals, i.e. said compound is 30 times less toxic than thiocolchicine). It is also active against many viruses.

The therapeutical agent of the present invention is notably administered under the form of gelules containing for example 0.1 mg of active component; the daily dosages for an adult human being are on the order of 0.1 to 0.8 mg, usually about 0.4 to 0.5 mg (i.e. 4 or 5 gelules).

The extremely low toxicity of the present derivative of colchicine, referred to hereinafter as "new derivative" (the high toxicity is about 3,000 times less than that of colchicine), its obvious anti-mitotic activity (equal to if not stronger than that of colchicine) as well as its non-negligible anti-gout properties would make a potentially interesting substance thereof.

The pharmacological properties of the new derivative will be studied in detail through comparison with colchicine itself.

I — ANTI-GOUT EFFECT

1. Preliminary remarks
   a. Inhibition of Phagocytosis

The capability of colchicine in relieving pain in case of gout seems to be mainly due to an inhibition of phagocytosis. Accordingly, colchicine does not exert any effect upon the precipitation of uric acid, but reduces inflammation due to crystals deposited through the mechanism described hereinafter.

When crystals are present in the synovial liquid there is found a leucocytic infiltration followed by a reaction through phagocytosis which starts with polymorphonuclear leucocytes; this reaction gives rise through metabolic activation to a local accumulation of lactic acid. This accumulation yields an acid pH which will promote the deposit of uric acid. These successive phenomena of crystallization, leucocytic infiltration, phagocytosis and increased metabolic activity would correspond to a vicious circle.

Colchicine by decreasing phagocytosis would be conducive to stop such a vicious circle.

Inhibition of phagocytosis due to colchicine and to the new derivative has therefore been investigated under the conditions stated in paragraph (2) set forth hereinafter by using cultures of macrophages of mice.

b. Anti-gout activity with the rat

The anti-gout activity has also been studied "in vivo" with the rat by investigating the inhibition of oedema induced in the hind paw through local injection of sodium urate.

2. Inhibition of Phagocytosis
   a. Methods

Cultures of peritoneal macrophages of mice have been prepared in Applicant's laboratories according to a thoroughly tried and tested process briefly described hereinafter. The macrophages the proliferation of which in the animal has been previously stimulated in vivo by an intraperitoneal injection of proteose-peptone (Difco) are collected or gathered in a sterile manner by washing the peritoneal cavity. They are then suspended in a culture medium consisting of a basal Eagle medium (B-D Mérieux) admixed with 20 % of serum of foetal calf (Flow Laboratories) and with 100 U/ml of penicillin and of 50 µg/ml of streptomicin. They are distributed at the rate of $5 \times 10^6$ cells per dish into Petri Falcon dishes of 35 mm in diameter wherein they will form a monocellular layer. They are cultivated at 37° C in a water-saturated atmosphere of air and of 5 % carbon dioxide $CO_2$.

For the measurement of phagocytosis 48 hours cultures (experiments I, II, IV) or 72 hours cultures (experiments II, V) have been used. Each culture has been allowed to undergo incubation for 80 minutes with amounts of colchicine or of the derivative ranging from 0.004 µg to 40 µg. Colchicine and its derivative have been dissolved in methanol. The volume of methanol added to each culture was equal to 10 µl except for experiment I (25 µl).

For the phagocytosis, opsonized red blood-corpuscles have been used; they have been added to the cultures of macrophages 10 minutes after the admixture of colchicine or of its derivative.

b. Results

The results obtained are listed in table 1 annexed herewith. It may be noted that the effect of colchicine and that of the derivative upon inhibition of phagocytosis are very similar: both substances will inhibit phagocytosis depending upon the dose. Inhibition is indeed equal to 15 % and 10 %, respectively, with amounts of colchicine and of the derivative equal to 0.004 µg and to 65 % with amounts of colchicine and of the derivative equal to 4 μg. It may be noted that with amounts higher than 4 μg the percentage of inhibition of phagocytosis does not increase any more; with 40 μg it is equal to 67 % for colchicine and 62 % for its derivative.

The results obtained with colchicine are rather similar to those described in the literature which reports the following inhibition of phagocytosis:

| μg of colchicine | % phagocytosis |
|---|---|
| 0.004 | 68.6 ± 3.7 |
| 0.04 | 54.2 ± 5.4 |
| 0.4 | 39.8 ± 1.2 |

This study has shown that the derivative will inhibit phagocytosis of the red blood-corpuscles by the macrophages nearly as colchicine would do. The derivative would therefore seem also to exhibit an anti-gout activity but possibly a little smaller than colchicine at the least in the test carried out when both substances are compared to each other in terms of μg and not of μM.

3. Anti-gout activity with the rat a. Methods 8 g of uric acid (puriss Fluka A.G. Buchs S.G.) were added to 1,600 ml of boiling water and the pH of the solution was adjusted to 7.4 with 20 % of sodium hydroxyde NaOH. The solution was heated up to 95° C and allowed to cool down to the room temperature of the laboratory while being slightly stirred for 7 to 8 hours. The crystals of sodium urate were recovered through filtration on a Buchner filter and air-dried. The formation of crystals was confirmed through microscopic examination.

Sprague Dawely female rats having an average weight of 200 g were used for this investigation.

The oedema was produced through injection into the plantar arch of the left hind foot or leg of 0.1 ml of a suspension of crystals of sodium urate in a physiological salt solution (100 mg/ml). An equal volume of saline solution was injected into the right foot or leg as a control.

Colchicine and the derivative were dissolved in a 25–33 % ethanolic solution. Colchicine and the derivative in ethanolic solution were injected through the subcutaneous way.

Three injections with the same dose were carried out 0.2 and 4 hours after the injection of crystals of urate. The volume injected ranged from 3.5 to 6 ml/kg each time. The reference rats also received three injections of a solution containing the same concentration in ethanol.

Six hours after the injection of the crystals of urate, the rats were killed through decapitation, the hind legs were amputated at the ankle and weighed. The difference in weight between the left leg and the right leg yielded the measured extent of the oedema produced by the crystals of urate and the protection obtained by the treatment carried out.

b. Results

The results obtained with each group of animals: reference animals, animals having received 2 mg/kg of colchicine, 2 mg/kg or 6 mg/kg of the derivative are shown in table 2 annexed herewith.

It may be noted that there is provided a significant protection against the oedema produced by crystals of urate when using a dose of colchicine of 2 mg/kg and a dose of the derivative of 6 mg/kg.

II ANTI-MITOTIC ACTIVITY

1. Preliminary remarks

It is known that colchicine acts upon the microtubules.

The following assumption is now widely accepted. Colchicine, by specifically linking or bonding itself to the proteins of the microtubules destroys the organization of the mitotic spindle and accordingly stops the mitosis. Moreover it would seem that this specific linking or bonding of colchicine to the proteins of microtubules is responsible not only for its anti-mitotic activity but also for its anti-gout activity.

The following study is dealing with the anti-mitotic activity of colchicine and of the new derivative upon cultures of lymphocytes stimulated by phyto-hemagglutinin. The stimulation of lymphocytic mitosis may be expressed by two parameters which are the synthesis of DNA and the mitotic index, respectively. The former is given by the measurements of incorporation of tritiated thymidin; the latter by the counting of the mitotic figures. In this report only the first parameter has been investigated.

2. Anti-mitotic activity upon (in vitro) cultures of human leucocytes

Three experiments have been carried out by using the blood of three different voluntary subjects, namely two men and a woman.

a. Preparation of the cultures of leucocytes 200 ml of blood of each volunteer have been collected on heparin.

To 100 ml of blood have been added 20 ml of a sterile physiological solution containing 4.5 % of dextran T500, dextran serving to remove most of the red blood-corpuscles.

After a sedimentation for 30 minutes, the supernatant matter is taken off and centrifuged for 10 minutes at 1,200 rpm (400 g) and thereby are obtained the leucocytes in the centrifugation button or residue and the platelets in the supernatant matter.

The leucocytes obtained are washed twice with a sterile physiological solution and centrifuged at 1,200 rpm in order to remove any trace of dextran therefrom. They are then suspended again in a known volume (3 ml) of physiological solution for being counted and are eventually subjected to another centrifugation.

The leucocytes are again suspended in a plasma/culture medium (volumetric ratio = 8/28) in order to yield a final concentration of $1.2 \times 10^6$ cells per ml.

The plasma has been obtained through centrifugation at 2,000 rpm of the 100 ml of blood not yet used out of the 200 ml taken off.

The culture medium is prepared in the following manner.

To 100 ml of MEM (TC Minimal Medium Eagle, Difco):

1 cm³ of TC Penicillin-Streptomicin Difco
0.73 cm³ of Glutamine Difco
0.94 cm³ of Liquemine Roche
0.16 cm³ of Phytohemagglutinin Difco (PHA).

b. Experimentation with colchicine and its derivative

The suspension of leucocytes in the plasma/culture medium mixture is distributed into 29 tubes. Into 20 of these tubes are added 5 (6) different concentrations of colchicine or of its derivative.

Colchicine and its derivative are dissolved in methanol and added to the tubes containing the suspension of leucocytes at the rate of (2.5), 5, 10, 20, 30, 50 μg per ml of suspension. For each concentration 2 tubes have been filled which would represent the 20 tubes. Among the 9 other prepared tubes, 4 have been used as controls, i.e. without any admixture of substance and 5 have served to study the effects of the different amounts of methanol upon the leucocytes.

All the tubes closed only by means of a stopper plug of sterile gauze are started to be cultivated at 37° C in a water-saturated atmosphere of air and of 5 % carbon dioxide $CO_2$ for 48 hours.

Once this period has lapsed, 1 $\mu$Ci of thymidine marked with $^3$H radio-isotope is added to each tube and one would wait again for 48 hours.

Centrifugation is carried out at 2,000 rpm for 15 minutes and the precipitate is washed with methanol. Then the precipitate from each tube is made dissolvable with 0.2 ml of soluene (Packard) at 40° C.

The dissolved precipitate is transferred from each tube into scintillation bottles and the radio-activity is measured by using Instagel (Packard) as a scintillating mixture.

c. Results

The results obtained are shown in table 3.

It may be noted that, in these three experimentations increasing amounts of colchicine the anti-mitotic power or capacity of which is well-known would decrease the incorporation of radio-activity into the precipitate of the proteins and nucleic acids, i.e. they are inhibiting the synthesis of DNA. The anti-mitotic activity is already very substantial from 2.5 $\mu$g/ml at which concentration the derivative shows a similar or higher activity. With higher concentrations, the derivative seems to have still more effect than colchicine; however at higher concentrations cytotoxicity phenomena are occurring (see section 4) and may be misleading for the evaluation of the anti-mitotic activity.

Therefore, the comparison of the anti-mitotic activity between colchicine and its derivative should rather be made at concentrations lower than or equal to 2.5 $\mu$g/ml.

A fourth experimentation has accordingly been effected in order to use concentrations of colchicine and of the derivative in the culture medium lower than 2.5 $\mu$g/ml (0.5 and 1 $\mu$g/ml). For this experimentation, a voluntary woman has given 50 ml of blood; then it has been proceeded in a slightly modified way with respect to that described hereinabove, i.e. the leucocytes have been started to be cultivated only with PHA for 48 hours (without colchicine or the derivative) and thereafter the various amounts of colchicine and of the derivative have been added and left into the cultures for 6 hours. After that time has lapsed, thymidine-$^3$H has been added and left in contact for 18 hours.

The results obtained are shown in table 4 annexed herewith. It may be noted that even at lower concentrations colchicine and the derivative exhibit a definite anti-mitotic activity, which activity seems moreover be markedly stronger with the derivative than with colchicine.

The results of this fourth experimentation are particularly interesting as the concentrations of colchicine and of the derivative used are very much lower than those likely to give rise to phenomena of cytotoxicity.

3. Anti-mitotic activity upon cultures of leucocytes from rats (after having given colchicine or the derivative to the animals)

A dose of 2 mg/kg of colchicine or of the derivative (in propylene-glycol) was given through the oral tract to Sprague Dawley SIV 50 he-rats having a weight of 150 – 200 g.

Two groups of animals serve as a control namely one group which has been given no substance and another group which has been given a volume (7.5 ml/kg) of propylene-glycol identical with that received by the treated animals.

Blood (about 0.2 ml) obtained through puncture of the retro-orbital veinous sinus was collected under sterile conditions prior to the administration of the substances and 6 hours later.

Then one proceeded with carrying out a micro-culture of the leucocytes in the presence of phytohemagglutinin.

The results shown in table 5 annexed herewith are reproducing on the one hand the amount of lymphocytes cultivated and on the other hand the amount of radio-activity embodied into the precipitate of the proteins and of the nucleic acids of each culture and finally the immunity response, i.e. the radio-activity embodied by the number of lymphocytes cultivated.

6 hours after the beginning or initiation of the experiment whether with reference animals or with treated animals a decrease in the number of lymphocytes may be noted.

III HIGH TOXICITY WITH THE RAT

The high toxicity of the new derivative of colchicine (N-desacetyl-N-adamantoyl-thiocolchicine) has been investigated through the oral way with the male and female Sprague Dawley SIV 50 rat having an average weight of 100 g.

Two experiments have been carried out. In the first one, only the high toxicity of the derivative has been studied; in the second one, the high toxicity of the derivative has been compared with that of colchicine.

The derivative and colchicine have been administered in suspension in propylene glycol through an oesophageal tube at the rate of 2 ml per rat for the first experiment and of 1 ml for the second one.

The animals have been observed for 10 days.

The results of the first and of the second experiments are listed in the accompanying tables 6 and 7, respectively.

According to the literature, the $LD_{50}$ of colchicine with the mouse through the intraperitoneal path is 1 mg/kg. Moreover the lethal dose with a man may sometimes be of 6 mg only. With the rat the $LD_{50}$ of colchicine through the intraveinous path is 1.7 mg/kg and with the cat still through the intraveinous path equal to 0.25 mg/kg.

The low toxicity of the derivative is therefore surprising (at a dose of 3 g/kg no death has been detected).

IV CYTOTOXICITY WITH RESPECT TO THE LYMPHOCYTES

1. Cytotoxicity upon in vitro cultures of human leucocytes (stimulated by PHA)

The cytotoxicity has been investigated on human leucocytes by means of the viability test with Trypan blue.

a. In a first experimentation cultures of leucocytes of a voluntary man were prepared and caused to undergo incubation with phytohemagglutinin (PHA) and with different concentrations of colchicine or of its derivative ($C_1 = 2.5$ $\mu$g/ml of culture, $C_3 = 10$ $\mu$g/ml, $C_5 = 30$ $\mu$g/ml, $C_6 = 50$ $\mu$g/ml). Leucocytes only containing PHA served as controls.

After 3, 42, 68 and 72 hours of incubation a sample of each culture was contacted by a drop of Trypan blue and laid on a slide of a microscope. Then took place the counting of the dead cells (those with assumed an orange colour) and of all the cells present on the slide in order to obtain the ratio of the number of dead cells to the total number of cells. The results expressed as a rate in per cent are shown in the accompanying table 8.

It may be noted that the cytotoxicity of colchicine and that of the derivative are substantially the same with a concentration ($C_1$) of 2.5 µg/ml and it begins to differentiate with a concentration ($C_3$) of 10 µg/ml. On the other hand, with higher concentrations the derivative seems to be more cytotoxic than colchicine itself.

During this first experimentation on cytotoxicity before carrying out the test with Trypan blue, the leucocytes which have been incubated for 72 hours with PHA, colchicine or its derivative have been counted.

The results set forth in table 9 show that the number of leucocytes decreases with increasing amounts of colchicine but is still further lowered with the same amounts of the derivative.

b. After the experimentation which has just been described, the study of cytotoxicity has been continued with two other samples of human leucocytes still by means of the viability test with Trypan blue.

Cultures of leucocytes (I, II) from two other voluntary men were prepared and caused to undergo incubation with phytohemagglutinin and different concentrations of colchicine (C), of its derivative (D) or of the carboxy-1-adamantane fraction (A). Contrary to the previous experiment in which different volumes of a solution of a given concentration have been added, in this experiment the various concentrations were prepared through dilution of a concentrated solution in order to add a same volume of methanol to each culture. This volume was 50 µl and corresponded for colchicine and its derivative to:

$C_1$ = 2.5 µg/ml of culture
$C_3$ = 10 µg/ml of culture
$C_5$ = 30 µg/ml of culture
$C_6$ = 50 µg/ml of culture;

and for the carboxy-1-adamantane fraction to:

$C_3$ = 4.5 µg/ml of culture
$C_6$ = 22.5 µg/ml of culture.

Leucocytes only containing phytohemagglutinin and others containing phytohemagglutinin and 50 µl of methanol served as controls.

The percentage of dead cells was determined after different numbers of hours of incubation. The results for the cultures I and II are given in table 10 annexed herewith.

It may be noted that the cytotoxicity of colchicine with different concentrations is practically identical with that due to the methanol added to the refrence leucocytes.

With the derivative the cytotoxicity does not seem to be very different from that of colchicine or methanol after 23 hours of incubation; however for longer periods of time and more especially with concentrations $C_5$ and $C_6$ it becomes more substantial.

As to the carboxy-1-adamantane fraction, it seems to have no effect until 46 hours of incubation.

As to the counting of leucocytes (table 11 annexed herewith) which should be considered as being very approximative the number seems to remain substantially the same in the absence or in the presence of colchicine, of its derivative or of the carboxy-1-adamantane fraction.

2. Cytotoxicity on (in vitro) cultures of human leucocytes not stimulated with PHA Cultures of leucocytes originating from a voluntary woman were prepared as previously described, but without adding phytohemagglutinin. Different concentrations of colchicine or of the derivative were left in contact with the cultures for 6, 30 or 48 hours.

The concentrations of colchicine and of the derivative were prepared through dilution of a concentrated solution in order to add a same volume of methanol to each culture.

The doses were the following:

$C_1$ = 0.01 µg/ml of culture
$C_2$ = 0.1 µg/ml of culture
$C_3$ = 0.5 µg/ml of culture
$C_4$ = 1.0 µg/ml of culture
$C_5$ = 2.5 µg/ml of culture
$C_6$ = 10.0 µg/ml of culture.

Samples of culture with or without addition of methanol served as references.

The results set forth in the accompanying table 12 show that the leucocytes in the absence of any stimulation with phytohemagglutinin quickly have a tendency to die. Already after 30 hours of culture, 50 % of the cells are dead.

As to the cytotoxicity of colchicine or of its derivative, under the conditions used, it is practically zero. As a matter of fact, with an incubation time of 6 to 30 hours, the percentage of dead cells with any concentration does not differentiate from the controls. After 48 hours of culture, the percentage of dead cells is practically the same with colchicine and its derivative and moreover this percentage is slightly larger than with the controls.

It may therefore be concluded that with concentrations of colchicine or of the derivative ranging from 0.01 µg/ml to 10 µg/ml of culture and with exposition times extending up to 30 hours no cytotoxicity is detectable with colchicine or with the derivative.

3. Cytotoxicity on cultures of leucocytes from rats (after the animals were given colchicine or the derivative)

A dose of 2 mg/kg of colchicine or of the derivative (in 1.5 ml of propylene glycol) was administered through the oral path to Sprague Dawley SIV 50 he-rats having a weight of 150 to 200 g. These rats had been kept fasting from the evening before.

Two groups of rats served as references.

The first group consisted of rats which were given no substance. The second group consisted of rats which were given a same volume (7.5 ml/kg) of propylene glycol as that received by the treated animals.

During this experimentation a counting of the leucocytes as well as a leucocytic distribution were made before administration and 6 hours after administration of the substances. Moreover as a cytoxicity index, a measurement of the viability of leucocytes obtained 6 hours after administration was carried out by means of the staining test with Trypan blue.

The results of the three different experimentations set forth in table 13 annexed herewith are relating to the count of leucocytes per $mm^3$ before and after administration of the substances.

Six hours after the start of the experiment, a more or less significant decrease in the number of white blood-corpuscles could be noticed.

It is however not believed that the same may be ascribed to the administration of colchicine or of the derivative. As a matter of fact the same phenomenon has been observed with the references. The cause may be found in keeping the animals fasting as well as in the following fact: before the administration of the substances to each one of the animals about 1 ml of blood was collected which represents nearly one-tenth of its total volumic blood content. The blood content of the rat represents one-twentieth of the weight of the body. If the animal weighs about 200 g, the volumic blood content will be 10 ml.

As to the variation in the number of leucocytes from one animal to another it is of quite physiological character. The mean value described in the literature for an adult rat is indeed 9,000 leucocytes per $mm^3$ with a deviation of from 6,000 to 18,000 leucocytes per $mm^3$.

As to the leucocytic distribution shown in table 14 annexed herewith and which relates to the following normal values:

|  | X | deviation |
| --- | --- | --- |
| Neutrophiles with non segmented nuclei | 7 | 2 – 14 |
| Neutrophiles with segmented nuclei | 13 | 6 – 25 |
| Eosinophiles | 2 | 0 – 4 |
| Basophiles | <1 | 0 – 0 |
| Monocytes | 1 | 0 – 3 |
| Lymphocytes | 78 | 55 – 96 |

No difference between the beginning and the end of the experiment has been noted.

As to the viability of leucocytes determined on the blood collected 6 hours after the substances have been administered and the results of which are shown in table 15 no cytotoxic effect has been noticed for colchicine or its derivative.

Table 1

| μg of colchicine | % phagocytosis with respect to controls (= 100%) Experimentation | | | | |
| --- | --- | --- | --- | --- | --- |
|  | I | II | III | IV | V |
| & 0.004 |  |  | 87.6 | 81.6 |  |
| 0.04 |  |  | 65 | 78.9 | 79.5 |

Table 1-continued

|  | I | II | III | IV | V |
| --- | --- | --- | --- | --- | --- |
| 0.4 |  |  |  | 44.7 | 54.3 | 54.4 |
| 4 |  |  | 36.9 | 34.5 | 32.2 | 38.2 |
| 5 |  |  | 30.3 |  |  |  |
| 10 |  |  | 33.7 |  |  |  |
| 12.5 |  | 36.5 |  |  |  |  |
| 20 |  |  | 33.4 |  |  |  |
| 30 |  |  | 36.2 |  |  |  |
| 40 |  |  | 32.0 | 33.2 | 33.8 |  |
| & μg of derivative |  |  |  |  |  |  |
| & 0.004 |  |  |  | 93.8 | 85.8 |  |
| 0.04 |  |  |  | 84.5 | 85.9 | 89.9 |
| 0.4 |  |  |  | 72.8 | 77.6 | 76.2 |
| 4.0 |  |  | 22.5 | 33.1 | 42.5 | 39.3 |
| 5 |  |  | 25.9 |  |  |  |
| 10 |  |  | 25.5 |  |  |  |
| 12.5 |  | 46.2 |  |  |  |  |
| 20 |  |  | 31.3 |  |  |  |
| 30 |  |  | 31.1 |  |  |  |
| 40 |  |  | 31.0 | 43.7 | 48.4 |  |

Table 2

| Substance | Dose (mg/kg) | Number of animals | Difference (g) (Average ± standard deviation of mean term) | % of inhibition of edema | P |
| --- | --- | --- | --- | --- | --- |
| References |  | 25 | 0.292 ± 0.032 |  |  |
| Colchicine | 2 | 18 | 0.152 ± 0.019 | 48 | 0.005 |
| Derivative | 2 | 12 | 0.264 ± 0.031 | 10 | 0.60 |
| Derivative | 6 | 12 | 0.145 ± 0.019 | 50 | 0.005 |

Table 3

| Subjects | Colchicine μg/ml | cpm | Derivative μg/ml | cpm |
| --- | --- | --- | --- | --- |
| Volunteer Nr. 1 | 0 | 47,403 | 0 | 47,403 |
|  | 5 | 14,190 | 5 | 5,703 |
|  | 10 | 10,884 | 10 | 3,190 |
|  | 20 | 7,945 | 20 | 443 |
|  | 30 | 4,874 | 30 | 195 |
|  | 50 | 4,910 | 50 | 138 |
| Volunteer Nr. 2 | 0 | 19,649 | 0 | 19,649 |
|  | 2.5 | 8,103 | 2.5 | 5,359 |
|  | 5 | 8,756 | 5 | 4,035 |
|  | 10 | 6,046 | 10 | 1,766 |
|  | 20 | 8,477 | 20 | 926 |
|  | 30 | 8,136 | 30 | 435 |
|  | 50 | 5,384 | 50 | 193 |
| Volunteer Nr. 3 | 0 | 20,593 | 0 | 20,593 |
|  | 2.5 | 5,242 | 2.5 | 6,259 |
|  | 5 | 5,117 | 5 | 2,101 |
|  | 10 | 6,450 | 10 | 968 |
|  | 20 | 3,858 | 20 | 304 |
|  | 30 | 3,044 | 30 | 200 |
|  | 50 | 2,107 | 50 | 84 |

Table 4

|  | Colchicine μg/ml | cpm | Derivative μg/ml | cpm |
| --- | --- | --- | --- | --- |
| Volunteer Nr. 4 | 0 | 4,799 | 0 | 4,799 |
|  | 0.5 | 3,450 | 0.5 | 3,322 |
|  | 1 | 2,384 | 1 | 1,713 |

Table 5

| Groups of rats | before administration | | | 6 hours after administration | | |
| --- | --- | --- | --- | --- | --- | --- |
|  | Number of lymphocytes/ culture | embodied radioactivity cpm | cpm number of lymphocytes | Number of lymphocytes/ culture | embodied radioactivity cpm | cpm number of lymphocytes |
| Controls room | 150,360 | 2,280 | $1.52 \times 10^{-2}$ | clotted blood 92,620 | 17,426 | $18.81 \times 10^{-2}$ |
|  | 133,000 | 8,651 | $6.50 \times 10^{-2}$ |  |  |  |
|  | 225,000 | 15,471 | $6.88 \times 10^{-2}$ | 126,000 | 16,706 | $13.26 \times 10^{-2}$ |
|  |  | $x = 8,801 \pm 3,809$ | $x = 4.97 \times 10^{-2} \pm 1.73$ |  | $x = 17,066 \pm 360$ | $x = 16.03 \times 10^{-2} \pm 0.278$ |

Table 5-continued

| Groups of rats | before administration | | | 6 hours after administration | | |
|---|---|---|---|---|---|---|
| | Number of lymphocytes/ culture | embodied radioactivity cpm | cpm number of lymphocytes | Number of lymphocytes/ culture | embodied radioactivity cpm | cpm number of lymphocytes |
| Controls | 204,000 | 13,104 | $6.42 \times 10^{-2}$ | 124,000 | 7,944 | $6.41 \times 10^{-2}$ |
| Propylene glycol | 228,480 | 21,404 | $9.37 \times 10^{-2}$ | 130,020 | 21,464 | $16.51 \times 10^{-2}$ |
| | 175,960 | 2,808 | $1.60 \times 10^{-2}$ | 189,560 | 4,271 | $2.25 \times 10^{-2}$ |
| | | $x = 12,439 \pm 5,379$ | $x = 5.80 \times 10^{-2} \pm 2.26$ | | $x = 11,126 \pm 5,227$ | $x = 8.39 \times 10^{-2} \pm 4.23$ |
| Colchicine | 103,960 | 2,200 | $2.12 \times 10^{-2}$ | clotted blood | | |
| | 163,400 | 6,763 | $4.14 \times 10^{-2}$ | 148,200 | 7,453 | $5.03 \times 10^{-2}$ |
| | 156,400 | 16,740 | $10.70 \times 10^{-2}$ | 108,240 | 437 | $0.40 \times 10^{-2}$ |
| | | $x = 8,605 \pm 3,096$ | $x = 5.32 \times 10^{-2} \pm 1.86$ | | $x = 3,945 \pm 3,508$ | $x = 2.72 \times 10^{-2} \pm 2.32$ |
| Derivative | 132,480 | 7,384 | $5.57 \times 10^{-2}$ | 172,500 | 8,466 | $4.91 \times 10^{-2}$ |
| | 147,000 | 10,195 | $6.94 \times 10^{-2}$ | clotted blood | | |
| | 271,460 | 7,709 | $6.52 \times 10^{-2}$ | 244,760 | 8,690 | $3.55 \times 10^{-2}$ |
| | 257,060 | 13,619 | $5.30 \times 10^{-2}$ | 261,900 | 14,836 | $5.66 \times 10^{-2}$ |
| | | $x = 12,227 \pm 2,228$ | $x = 6.08 \times 10^{-2} \pm 0.39$ | | $x = 10,664 \pm 2,087$ | $x = 4.71 \times 10^{-2} \pm 0.62$ |

Table 6

| Substance | Number of animals | Dose (mg/kg) | Death rate |
|---|---|---|---|
| Derivative | 5 + 5 | 2,000 | 0/10 |
| | 5 + 5 | 3,000 | 0/10 |

Table 7

| Substance | Number of animals | Dose (mg/kg) | Death rate |
|---|---|---|---|
| Colchicine | 3 + 3 | 100 | 6/6* |
| | 3 + 3 | 500 | 6/6** |
| Derivative | 3 + 3 | 100 | 0/6 |
| | 3 + 3 | 500 | 0/6 |
| | 3 + 3 | 1,000 | 0/6 |
| | 3 + 3 | 2,000 | 0/6 |
| | 3 + 3 | 3,000 | 0/6 |

*1 rat dead after 24 hours, 5 rats dead after 48 hours
**5 rats dead after 24 hours, 1 rat dead after 48 hours Table 8

Study of cytotoxicity of colchicine (C) and of its derivative (D) of dead cells
% of dead cells

| Incubation period (hours) | Control | $C_1$ | $C_3$ | $C_5$ | $C_6$ | Colchicine (C) Derivative (D) |
|---|---|---|---|---|---|---|
| 3 | 1 | 1 | 1 | 0 | 0 | C |
| | | 0 | 0 | 0 | | D |
| 42 | 3 | 3 | 2 | 10 | 2 | C |
| | | 5 | 7 | 23 | 32 | D |
| 68 | 3 | 6 | 9 | 9 | 21 | C |
| | | 5 | 9 | 20 | very few cells | D |
| 72 | 9 | 7 | — | 18 | 24 | C |
| | | 9 | 12 | 35 | very few cells | D |

| | Count of leucocytes after 72 hours | | | | Colchicine (C) derivative (D) |
|---|---|---|---|---|---|
| Control | $C_1$ | $C_3$ | $C_5$ | $C_6$ | |
| 412,500 | 457,000 | 420,000 | 397,000 | 270,000 | C |
| 412,500 | 487,000 | 360,000 | 180,000 | 157,000 | D |

Table 10

Study of cytotoxicity of colchicine, of its derivative and of carboxy-1-adamantane
% of dead cells

| Incubation Period (hours) | Control | Control + Methanol | $C_1$ | $C_3$ | $C_5$ | $C_6$ | Colchicine(C) Derivative(D) |
|---|---|---|---|---|---|---|---|
| 4 | 5 | 10 | — | 6 | — | 9 | C |
| | | | — | 15 | — | 17 | D |
| 22 | 4 | 8 | — | 5 | — | 7 | C |

Culture I

Table 10-continued

Study of cytotoxicity of colchicine, of its derivative and of carboxy-1-adamantane % of dead cells

| | | | | | | | |
|---|---|---|---|---|---|---|---|
| | | | — | 12 | — | 22 | D |
| 46 | 14 | 28 | — | 24 | — | 19 | C |
| | | | — | 42 | — | 53 | D |
| 76 | 9 | 34 | — | 24 | — | 23 | C |
| | | | — | 40 | — | 62 | D |

| | | | II | | | | carboxy-1- (A) |
|---|---|---|---|---|---|---|---|
| | | | | | | | adamantane |
| 23 | 0 | 12*/9 | 3 | 4 | 5 | 7*/2 | C |
| | | | 8 | 11 | 16 | 11*/15 | D |
| | | | — | 18 | — | 14 | A |
| 46 | 6 | 7*/12 | 11 | 8 | 11 | 11*/12 | C |
| | | | 4 | 13 | 22 | 39*/28 | D |
| | | | — | 12 | — | 10 | A |
| 72 | 12 | 11*/12 | 13 | 14 | 18 | 17*/20 | C |
| | | | 26 | 41 | 43 | 61 | D |
| | | | — | 25 | — | 25 | A |

*x/x = 2 different tubes

Table 11

Count of leucocytes after 72 hours

Culture I

| Control | Control + Methanol | $C_1$ | $C_3$ | $C_5$ | $C_6$ | Colchicine(C) Derivative(D) |
|---|---|---|---|---|---|---|
| 630,000 | 600,000 | — | 550,000 | — | 610,000 | C |
| | | | 430,000 | | 515,000 | D |

Culture II

| | | | | | | Carboxy-1-(A) adamantane |
|---|---|---|---|---|---|---|
| | 195,000 | | | | 225,000 | |
| 340,000 | 265,000 | 240,000 | 295,000 | 205,000 | 330,000 | C |
| | | | | | 290,000 | |
| | | 140,000 | 200,000 | 245,000 | 345,000 | D |
| | | — | 215,000 | — | 230,000 | A |

Table 12

% of dead cells (Average of 2 determinations)

| Incubation Period (hours) | Control | Control + Methanol | $C_1$ | $C_2$ | $C_3$ | $C_4$ | $C_5$ | $C_6$ | Colchicine (C) Derivative (D) |
|---|---|---|---|---|---|---|---|---|---|
| 6 | 1 | 0 | 1 | 0 | 2 | 1 | 1 | 1 | C |
| | | | 1 | 1 | 0 | 1 | 1 | 1 | D |
| 30 | 50 | 54 | 55 | 68 | 54 | 59 | 60 | 46 | C |
| | | | 64 | 54 | 50 | 49 | 45 | 67 | D |
| 48 | 91 | 88 | 93 | 93 | 91 | 95 | 92 | 92 | C |
| | | | 93 | 95 | 91 | 94 | 88 | 91 | D |

Table 13

| | Leucocytes / mm³ | | | | | |
|---|---|---|---|---|---|---|
| | 1 | | 2 | | 3 | |
| | Before | After | Before | After | Before | After |
| | 11,950 | 8,650 | 7,600 | 6,750 | 7,000 | 4,875 |
| | 9,300 | 9,100 | 6,900 | 6,450 | 12,500 | 7,000 |
| | 8,250 | 8,150 | | | 12,750 | 7,750 |
| Controls room | | | | | | |
| | 8,100 | coagulated | 13,300 | coagulated | 13,600 | 7,750 |
| Controls | 6,900 | coagulated | 13,550 | 12,750 | 10,350 | 11,150 |
| Propylene glycol | 16,450 | 9,005 | 9,200 | 2,300 | 10,750 | 9,750 |
| | 10,300 | 6,150 | 10,100 | 3,050 | 12,850 | 6,850 |
| Colchicine | 16,600 | 9,500 | 9,000 | 7,950 | 10,750 | 9,750 |
| | 10,450 | 7,900 | 7,050 | 6,950 | 8,500 | coagulated |
| | 10,000 | 7,750 | 9,950 | 8,900 | 15,250 | 13,750 |
| Derivative | 9,050 | 9,050 | 5,900 | 5,400 | 13,250 | 13,500 |

Table 13-continued

| | Leucocytes / mm³ | | | | | |
|---|---|---|---|---|---|---|
| | 1 | | 2 | | 3 | |
| | Before | After | Before | After | Before | After |
| | 12,250 | 8,450 | 9,350 | coagulated | 7,200 | coagulated |
| | 17,525 | 9,350 | — | — | — | — |

Table 14

| | | Leucocytic distribution | | | | |
|---|---|---|---|---|---|---|
| | | Neutrophils with non-segmented nucleus | Neutrophils with segmented nucleus | Eosinophils | Basophils | Monocytes | Lymphocytes |
| Control room | before | 1 | 3 | 0 | 0 | 1 | 96 |
| | after | 3 | 5 | 0 | 0 | 1 | 91 |
| | | 0 | 14 | 0 | 0 | 2 | 84 |
| | | 0 | 19 | 0 | 0 | 4 | 77 |
| | | 3 | 9 | 0 | 0 | 0 | 88 |
| | | 2 | 8 | 1 | 0 | 1 | 88 |
| | | 3 | 13 | 1 | 0 | 3 | 80 |
| | | 0 | 12 | 0 | 0 | 1 | 87 |
| | | 2 | 37 | 0 | 0 | 2 | 59 |
| | | 0 | 33 | 0 | 0 | 2 | 65 |
| Propylene-Control | | 8 | 38 | 1 | 0 | 3 | 50 |
| Colchicine | | 18 | 16 | 0 | 0 | 2 | 64 |
| | | 2 | 18 | 1 | 0 | 1 | 78 |
| | | 3 | 11 | 0 | 0 | 1 | 84 |
| | | 0 | 3 | 1 | 0 | 2 | 94 |
| | | 1 | 6 | 0 | 0 | 1 | 92 |
| | | 2 | 12 | 1 | 0 | 2 | 83 |
| | | 3 | 16 | 0 | 0 | 0 | 81 |
| | | 0 | 11 | 0 | 0 | 2 | 87 |
| | | 1 | 17 | 0 | 0 | 0 | 84 |
| Derivative | | 2 | 12 | 0 | 0 | 2 | 84 |
| | | 1 | 5 | 0 | 0 | 0 | 94 |
| | | 0 | 8 | 0 | 0 | 2 | 90 |
| | | 0 | 18 | 0 | 0 | 0 | 82 |
| | | 5 | 12 | 0 | 0 | 1 | 82 |
| | | 0 | 13 | 0 | 0 | 1 | 86 |

Table 15

| | % of dead cells 3 animals per group | | |
|---|---|---|---|
| Controls room | Control propylene glycol | Colchicine | Derivative |
| 1 | — | 1 | 2 |
| 0 | — | 2 | 1 |
| 1 | 0 | 0 | 0 |

What we claim is:

1. A pharmaceutical composition having anti-mitotic and anti-gout activities consisting of an effective amount of an active ingredient of the formula:

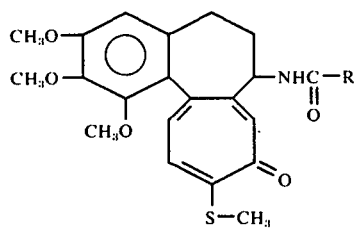

wherein R is an adamantyl radical, said derivative having the following characteristics: melting point 272.5°–273.5° C, specific rotation $[\alpha]_D^{20} = -200.0°$ (in chloroform; concentration 0.500 gr/1); and giving a solvation adduct with ethyl acetate; in admixture with a pharmaceutically acceptable carrier.

2. A pharmaceutical composition according to claim 1 wherein the active ingredient is present in from about 0.1 to 0.8 mg.

3. A thiocolchicine derivative of formula:

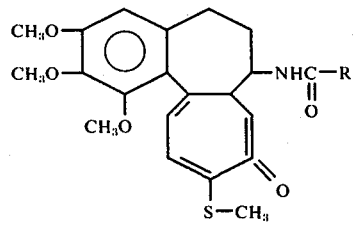

wherein R is an adamantyl radical, said derivative having the following characteristics: melting point: 272.5°–273.5° C; specific rotation $[\alpha]_D^{20} = -200.0°$ (in chloroform; concentration 0.500 gr/l); and gives a solvation adduct with ethyl acetate.

* * * * *